(12) United States Patent
Visser et al.

(10) Patent No.: US 8,518,923 B2
(45) Date of Patent: Aug. 27, 2013

(54) TREATMENT OR PREVENTION OF HYPERTENSIVE DISORDERS OF PREGNANCY OR FETAL GROWTH RETARDATION

(75) Inventors: Monique Visser, Zeist (NL); Herman Jan Tijmen Coelingh Bennink, Werkhoven (NL)

(73) Assignee: Pantarhei Bioscience B.V., Zeist (NL)

( * ) Notice: Subject to any disclaimer, the term of this patent is extended or adjusted under 35 U.S.C. 154(b) by 663 days.

(21) Appl. No.: 12/669,778

(22) PCT Filed: Jul. 14, 2008

(86) PCT No.: PCT/NL2008/050476
§ 371 (c)(1),
(2), (4) Date: Apr. 2, 2010

(87) PCT Pub. No.: WO2009/011576
PCT Pub. Date: Jan. 22, 2009

(65) Prior Publication Data
US 2010/0184731 A1    Jul. 22, 2010

(30) Foreign Application Priority Data
Jul. 19, 2007  (EP) .................................. 07112753

(51) Int. Cl.
*A61K 31/56*    (2006.01)
(52) U.S. Cl.
USPC ........................................................ 514/182
(58) Field of Classification Search
USPC ........................................................ 514/182
See application file for complete search history.

(56) References Cited

FOREIGN PATENT DOCUMENTS
| | | |
|---|---|---|
| EP | 1700602 A1 | 9/2006 |
| WO | WO 95/02408 A1 | 1/1995 |
| WO | WO 96/03929 A1 | 2/1996 |

OTHER PUBLICATIONS

Ros et al., American Journal of Medical Genetics, 2000;91:256-260.*

(Continued)

*Primary Examiner* — San-Ming Hui
(74) *Attorney, Agent, or Firm* — Gilberto M. Villacorta; Sunit Talapatra; Foley & Lardner LLP

(57) ABSTRACT

The present invention relates to the use of a steroid in the manufacture of a pharmaceutical composition for use in the therapeutic or prophylactic treatment of a hypertensive disorder of pregnancy (HDP) or fetal growth retardation, said treatment comprising administering to a female mammal a steroid selected from the group consisting of: substances represented by the following formula (formula I) in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms; precursors of such substances; and mixtures of one or more of the aforementioned substances and/or precursors.

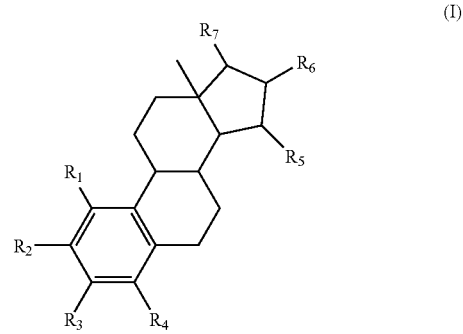

15 Claims, 1 Drawing Sheet

(56) References Cited

OTHER PUBLICATIONS

Figure 1:
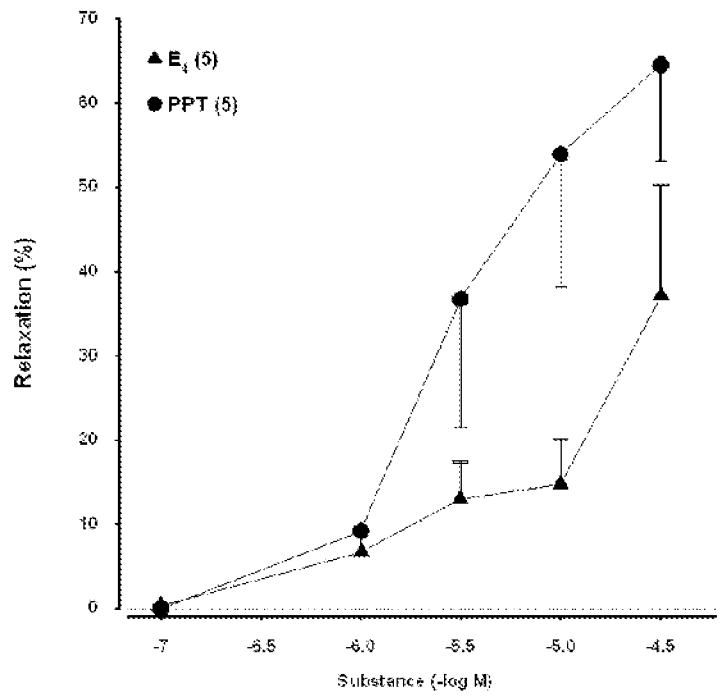

Tulchinsky, D. et al., "Plasma Estetrol as an Index of Fetal Well-Being" Journal of Clinical Endocrinology and Metabolism, Endocrine Society, Chevy Chase, MD, US, vol. 40, Jan. 1975, pp. 560-567.

International Search Report corresponding to PCT/NL2008/050476, dated Mar. 11, 2008, 2 pages.

* cited by examiner

TREATMENT OR PREVENTION OF HYPERTENSIVE DISORDERS OF PREGNANCY OR FETAL GROWTH RETARDATION

CROSS-REFERENCE TO RELATED APPLICATIONS

This application is a National Stage application of PCT/NL2008/050476, filed Jul. 14, 2008, which claims the benefit and priority of European Patent Application No. 07112753.4, filed Jul. 19, 2007. The foregoing applications are incorporated by reference herein in their entirety.

TECHNICAL FIELD OF THE INVENTION

The present invention relates to the treatment or prevention of hypertensive disorders of pregnancy (HPD) or fetal growth retardation.

BACKGROUND OF THE INVENTION

Hypertensive disorders of pregnancy and fetal growth retardation have in common that they are associated with insufficient blood supply through the arteria uterina. Another thing these disorders have in common is that at present they are very difficult to treat.

Examples of hypertensive disorders of pregnancy include hypertensive disorders from the group consisting of preeclampsia, eclampsia, HELLP syndrome and gestational or pregnancy-induced hypertension. All of these hypertensive disorders are believed to be associated with insufficient blood supply through the arteria uterina.

WO95/02408 teaches to employ a combination of a progestin and a nitric oxide synthase substrate in the treatment of preeclampsia and preterm labour. It is observed in the international patent application that preeclampsia, toxemia or eclampsia of pregnancy can be a significant health problem during pregnancy and they are the leading causes of fetal growth retardation, fetal mortality and morbidity, premature birth and maternal mortality.

Fetal growth retardation (or intrauterine growth retardation (IUGR)) implies that fetal growth is insufficient and that the fetus does not attain its growth potential. Thus, an IUGR fetus or newborn is characterized by too low body weight for gestational age (small-for-date). Fetal growth retardation has been associated with sub-optimal blood supply through the arteria uterina.

SUMMARY OF THE INVENTION

The inventors have unexpectedly discovered that steroids such as estetrol are capable of substantially enhancing the blood flow through the arteria uterina, especially in case the blood flow through this artery is limited as a result of vasoconstriction.

Control arteries are to be distinguished from transport arteries such as the aorta and the arteria pulmonalis. Unlike transport arteries, control arteries regulate the blood supply to organs. If control arteries are unduly constricted, blood supply to an organ may be impeded to such an extent that undesirable effects are elicited. For instance, in case of the arteria uterina, vascular constriction in pregnant females can cause hypertensive disorders of pregnancy and/or fetal growth retardation.

Tulchinsky et al. (J Clin Endocrinol Metab. 1975 April; 40(4):560-567) report that estetrol is considered to be a specific product of fetal liver and has been suggested as a good indicator of fetal well-being. In this article the authors conclude that plasma estetrol appears to be a good indicator of fetal well-being in patients with hypertensive disease of pregnancy.

The present inventors have recognized that the steroids of the present invention may advantageously be used to prevent or reduce high blood pressure in case of hypertensive disorders of pregnancy (HPD). In addition, these same steroids may suitably be employed to prevent or treat fetal growth retardation. As explained herein before, the inventors believe that the effectiveness of the present steroids in the treatment of HPD and fetal growth retardation is associated with the capability of these steroids to substantially enhance the blood flow through the arteria uterina, and possibly other control arteries such as arteria renalis, arteria hepatica and arteria mesenterica.

The steroids that are employed in accordance with the present invention are represented by the following formula

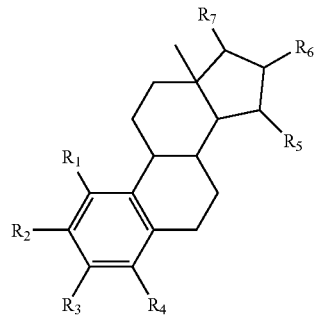

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms.

DETAILED DESCRIPTION OF THE INVENTION

Accordingly, the present invention relates to the use of a steroid in the manufacture of a pharmaceutical composition for use in the therapeutic or prophylactic treatment of a hypertensive disorder of pregnancy (HDP) or fetal growth retardation, said treatment comprising administering to a female mammal a steroid selected from the group consisting of: substances represented by the following formula

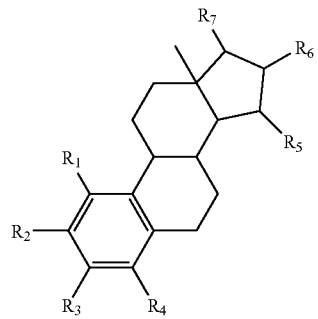

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms;

precursors capable of liberating a substance according to the aforementioned formula when used in the present treatment, which precursors are derivatives of the aforementioned steroids wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranol; or a straight or branched chain glycosidic residue containing 1-20 glycosidic units per residue; and mixtures of one or more of the aforementioned substances and/or precursors.

In a preferred embodiment of the present invention the steroid contains 4 hydroxyl groups. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The steroids according to the formula encompass various enantiomers since the carbon atoms that carry hydroxyl-substituents $R_5$, $R_6$ and $R_7$ are chirally active. In one preferred embodiment, the present steroid is 15α-hydroxy substituted. In another preferred embodiment the substance is 16α-hydroxy substituted. In yet another preferred embodiment, the substance is 17β-hydroxy substituted. Most preferably the steroids are 15α,16α,17β-trihydroxy substituted.

In a preferred embodiment of the present invention $R_3$ represents a hydroxyl group or an alkoxy group. In another preferred embodiment the groups $R_1$, $R_2$ and $R_4$ represent hydrogen atoms, in which case, if $R_3$, $R_5$, $R_6$ and $R_7$ are hydroxyl groups, the substance is 1,3,5 (10)-estratrien-3,15, 16,17-tetrol. A preferred isomer of the latter substance is 1,3,5 (10)-estratrien-3,15α,16α,17β-tetrol (estetrol).

Preferably, the steroid applied as the active component in the present composition is a so called biogenic estrogen, i.e. an estrogen that occurs naturally in the human body, a precursor of a biogenic estrogen or a mixture thereof. Because biogenic estrogens are naturally present in the fetal and female body, side-effects are not expected to occur, particularly not if the serum levels resulting from the exogenous administration of such estrogens do not substantially exceed naturally occurring concentrations. Naturally occurring steroids typically exhibit a 8β, 9α, 13β, 14α configuration of the steroid-skeleton.

Typical examples of precursors which can suitably be used in accordance with the invention are esters that can be obtained by reacting the hydroxyl groups of the estrogen substances with substances that contain one or more carboxy ($M^{+-}OOC-$) groups, wherein $M^+$ represents a hydrogen or (alkali)metal cation. Hence, in a particularly preferred embodiment, the precursors are derivatives of the estrogen substances, wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms.

The present treatment may suitably be used to treat humans, cattle, sheep, pigs, goat, horses as well as pets such as dogs and cats. Most preferably the present treatment is used to treat humans.

The present treatment may suitably employ enteral or parenteral administration of the steroid. The term "parenteral administration" as used in here encompasses transdermal, intravenous, intranasal, intravaginal, pulmonary, buccal, subcutaneous, intramuscular and intra-uterine administration. The term "enteral administration" includes oral as well as rectal administration.

Preferably the mode of administration is selected from the group consisting of intravenous, intravaginal, rectal, subcutaneous, intramuscular, intra-uterine or oral administration. More preferably the mode of administration is selected from the group consisting of intravaginal, subcutaneous, intramuscular or oral administration. In a particularly preferred embodiment the present treatment employs oral or intravaginal administration. Most preferably, the present treatment employs oral administration.

In accordance with the present treatment the steroid is usually administered in an amount of less than 2 mg per kg of bodyweight per day, preferably of less than 1 mg per kg of bodyweight per day. In order to achieve a significant impact from the administration of the steroid, it is advisable to administer in an amount of at least 2.5 µg per kg of bodyweight per day. Preferably, the administered amount is at least 5 µg per kg of bodyweight per day.

The present treatment comprises administering to a mammal in need of such treatment an effective amount of the steroid. The amount needed to be effective will differ from individual to individual and is determined by factors such as body weight, route of administration and the efficacy of the particular steroid used.

In the present treatment, particularly when used in humans, the steroid is usually administered in an average dosage of between 0.1 and 100 mg per day, preferably of between 0.5 and 50 mg per day.

Examples of hypertensive disorders of pregnancy that may be treated in accordance with the present invention include preeclampsia, eclampsia, HELLP syndrome and gestational hypertension. The present treatment is particularly suitable for treating or preventing preeclampsia.

Eclampsia is a serious complication of pregnancy and is characterised by convulsions. Usually eclampsia occurs after the onset of pre-eclampsia though sometimes no pre-eclamptic symptoms are recognisable. The convulsions may appear before, during or after labour, though cases of eclampsia after just 20 weeks of pregnancy have been recorded. Eclampsia can be fatal to both mother and fetus, with just under one in 50 affected women and one in 14 fetuses of affected women dying despite best-available medical care.

Preeclampsia (or pre-eclampsia) is a medical condition where hypertension arises in pregnancy (pregnancy-induced hypertension) in association with significant protein in the urine. If left untreated, preeclampsia can often rapidly progress to eclampsia. Pre-eclampsia may develop at varying times within pregnancy and its progress differs among patients; most cases are diagnosed pre-term. It has no known cure apart from ending the pregnancy by delivery of the fetus (induction of labor or abortion). It may also occur up to six weeks post-partum. It is the most common, dangerous complication of pregnancy and it may affect both the mother and the fetus.

Pre-eclampsia is diagnosed when a pregnant woman develops high blood pressure (two separate readings taken at least 6 hours apart of 140/90 or more) and 300 mg of protein in a 24-hour urine sample (proteinuria).

Some women develop high blood pressure without the proteinuria (protein in urine); this is called gestational hypertension or pregnancy-induced hypertension (PIH). Both pre-eclampsia and gestational hypertension are regarded as very serious conditions and require careful monitoring of mother and baby.

HELLP syndrome is another life-threatening obstetric complication considered by many to be a variant of preeclampsia. Both conditions occur during the latter stages of pregnancy, or sometimes after childbirth. HELLP is an abbreviation of the main findings:

Hemolytic anemia
Elevated Liver enzymes and
Low Platelet count

Often, a patient who develops HELLP syndrome has already been followed up for gestational hypertension, or is suspected to develop pre-eclampsia (high blood pressure and proteinuria). Up to 8% of all cases present after delivery. If the patient gets a seizure or coma, the condition has progressed into full-blown eclampsia.

The present treatment is advantageously used to treat or prevent hypertensive disorders of pregnancy and/or retarded fetal growth in a female mammal that is at least 20 weeks pregnant, preferably at least 24 weeks pregnant and most preferably 28 weeks pregnant.

In case of treatment of hypertensive disorders of pregnancy it is highly advantageous if the steroid is administered within 24 hours, preferably within 4 hours and most preferably within 60 minutes after the female mammal was found to suffer from hypertension. The sooner treatment is started after hypertension has been diagnosed, the lower the risk that pre-eclampsia, HELLP syndrome or gestational hypertension will evolve in eclampsia. In accordance with the present invention, hypertension is diagnosed if two separate readings taken at least 6 hours apart have shown a blood pressure of 140/90 or more.

The present treatment may comprise co-administration of other medicaments such as antihypertensive compounds. The present treatment preferably does not utilise co-administration of progestogens, cyclooxygenase inhibitors, nitric oxide donors, nitric oxide substrates, endothelin antagonist, endothelin synthase inhibitor, prostacyclin, prostacyclin analog, citrulline or citrulline analog.

Most preferably, the present treatment does not comprise co-administration of another pharmaceutically active component besides the steroid(s) according to the present invention.

The invention is further illustrated by means of the following examples.

EXAMPLES

Example 1

To evaluate acute dilatory responses to estetrol in human vasculature ex-vivo, the following study has been conducted.

Myometrial arteries and subcutaneous arteries (diameter: 220 μm; length: 2-3 mm) were dissected from normal pregnant women undergoing planned caesarian section. Myometrial arteries are present in the uterus and are branches from the arteria uterina.

Cigarette smokers and women with hypertension, diabetes mellitus, clinical manifestations of arteriosclerosis (CHD, peripheral artery disease, cerebrovascular disease), venous thromboembolic disease, liver disorders, unexplained vaginal bleeding, and personal or family history of breast cancer were excluded. None had received HRT, other steroid hormones, or any medication known to affect lipoprotein metabolism or blood pressure.

The dissected arteries were mounted on a pressure myograph (LSI, USA). The organ bath was perfused (7 ml/min) with PSS (mM: NaCl 119, KCl 4.7, $CaCl_2$ 2.5, $MgSO_4$ 1.17, $NaHCO_3$ 25, $KH_2PO_4$ 1.18, EDTA 0.026 and glucose 5.5; pH 7.4, 37° C., gassed with 5% $CO_2$ in $O_2$).

Arteries were discarded if they failed to maintain pressure, demonstrated incomplete occlusion of the lumen in response to extraluminal norepinephrine (NE, 10-6M in potassium substituted PSS (KPSS, 64 mM KCl in PSS) or failed to relax to bradykinin (BK, 10-6M).

Relaxation responses of estetrol and PPT ([1H]-pyrazole-1,3,5-tri-trisphenol, a selective estrogen-alpha-receptor agonist) in myometrial arteries and in subcutaneous arteries were compared. PPT was used as positive control. In a previous study it had been demonstrated that the estrogenic steroid estradiol was not capable of inducing relaxation in myometrial and subcutaneous arteries.

FIG. 1 depicts the response curve of estetrol and PPT in the myometrial arteries. The number of subjects is mentioned in parenthesis. The myometrial arteries were comparable in size (284±41, n=5 for estetrol versus 295±37, n=5 for PPT).

Figure 2:
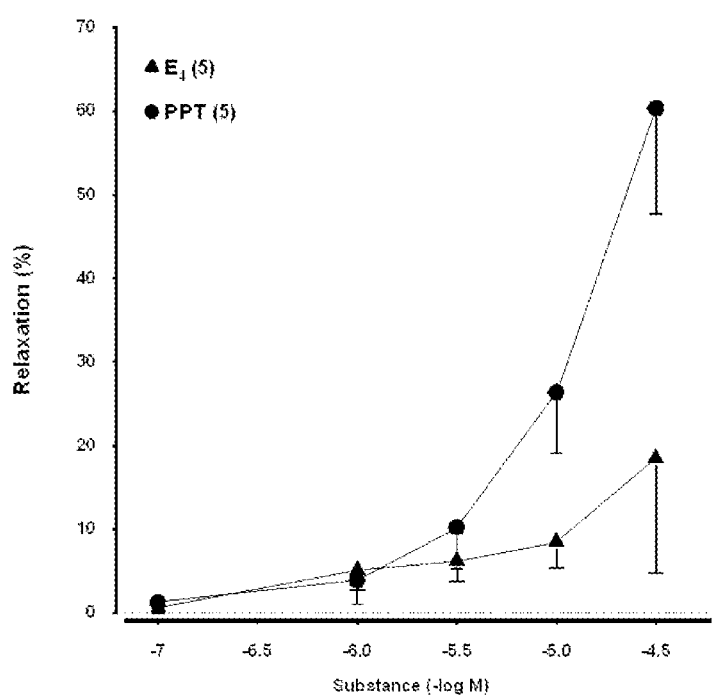

FIG. 2 depicts the response curve of estetrol and PPT in the subcutaneous arteries. Again, the number of subjects is mentioned in parenthesis. The subcutaneous arteries were comparable in size (213±21, n=5 for estetrol versus 194±25, n=5 for PPT).

The concentration response depicted in FIGS. 1 and 2 show that both the control compound (PPT) and estetrol are capable of inducing relaxation in myometrial and subcutaneous arteries. Surprisingly, estetrol appears to have a selective effect, because relaxation appeared to be more pronounced in the myometrial arteries compared to the subcutaneous arteries.

The invention claimed is:

1. A method of treating a hypertensive disorder of pregnancy (HDP) or fetal growth retardation, said method comprising administering to a female mammal a steroid selected from the group consisting of:
    (a) substances represented by the following formula

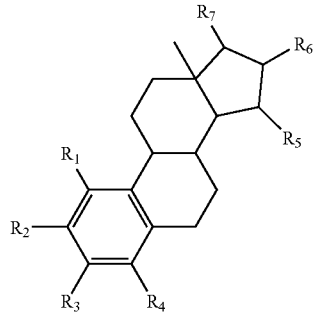

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; no more than 3 of $R_1$, $R_2$, $R_3$, $R_4$ are hydrogen atoms;
    (b) precursors capable of liberating a substance according to the aforementioned formula when used in the present method, which precursors are derivatives of the aforementioned steroids wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residue; and
    (c) mixtures of one or more of the aforementioned substances and/or precursors.

2. The method according to claim 1, wherein $R_3$ represents a hydroxyl group or an alkoxy group.

3. The method according to claim 1, wherein at least 3 of the groups $R_1$, $R_2$, $R_3$ and $R_4$ represent hydrogen atoms.

4. The method according to claim 1, wherein the hypertensive disorder of pregnancy is selected from the group consisting of preeclampsia, eclampsia, HELLP syndrome and gestational hypertension.

5. The method according to claim 3, wherein the hypertensive disorder of pregnancy is preeclampsia.

6. The method according to claim 3, wherein the steroid is administered within 24 hours of diagnosis of hypertension.

7. The method according to claim 1, wherein the administering is intravenous, intravaginal, rectal, subcutaneous, intramuscular, intra-uterine or oral.

8. The method according to claim 1, wherein the female mammal is pregnant.

9. The method according to claim 7, wherein the female mammal is at least 20 weeks pregnant.

10. The method according to claim 1, wherein the treatment does not comprise co-administration of progestogens, cyclooxygenase inhibitors, nitric oxide donors, nitric oxide substrates, endothelin antagonist, endothelin synthase inhibitor, prostacyclin, prostacylin analog, citrulline or citrulline analog.

11. The method according to claim 9, wherein the treatment does not comprise co-administration of another pharmaceutically active component besides the steroid.

12. The method according to claim 1, wherein the steroid is administered in a dosage of at least 2.5 μg per kg of bodyweight.

13. The method according to claim 11, wherein the steroid is administered in a dosage of at least 5 μg per kg of bodyweight.

14. A method of lowering the risk of a hypertensive disorder of pregnancy (HDP) or fetal growth retardation, comprising administering to a female mammal a steroid selected from the group consisting of:

(a) substances represented by the following formula

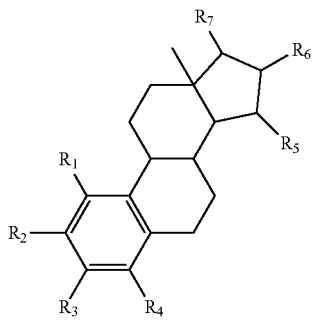

in which formula $R_1, R_2, R_3, R_4$ independently are a hydrogen atom, a hydroxyl group or an alkoxy group with 1-5 carbon atoms; each of $R_5, R_6, R_7$ is a hydroxyl group; no more than 3 of $R_1, R_2, R_3, R_4$ are hydrogen atoms;

(b) precursors capable of liberating a substance according to the aforementioned formula when used in the present method, which precursors are derivatives of the aforementioned steroids wherein the hydrogen atom of at least one of the hydroxyl groups has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residue; and (c) mixtures of one or more of the aforementioned substances and/or precursors.

15. The method according to claim 14, wherein the hypertensive disorder of pregnancy is selected from the group consisting of preeclampsia, eclampsia, HELLP syndrome and gestational hypertension.

* * * * *